(12) United States Patent
Iino et al.

(10) Patent No.: US 9,788,557 B2
(45) Date of Patent: Oct. 17, 2017

(54) LACTOBACILLUS CLASSIFIED AS LACTOBACILLUS PLANTARUM, AND USE THEREOF

(75) Inventors: Tohru Iino, Tokyo (JP); Norie Masuoka, Tokyo (JP); Fumiyasu Ishikawa, Tokyo (JP); Koichi Yoshimura, Tokyo (JP); Eiji Hayashida, Tokyo (JP)

(73) Assignee: Kabushiki Kaisha Yakult Honsha, Tokyo (JP)

( * ) Notice: Subject to any disclaimer, the term of this patent is extended or adjusted under 35 U.S.C. 154(b) by 936 days.

(21) Appl. No.: 13/636,072

(22) PCT Filed: Mar. 15, 2011

(86) PCT No.: PCT/JP2011/056065
§ 371 (c)(1),
(2), (4) Date: Nov. 30, 2012

(87) PCT Pub. No.: WO2011/115114
PCT Pub. Date: Sep. 22, 2011

(65) Prior Publication Data
US 2013/0064928 A1 Mar. 14, 2013

(30) Foreign Application Priority Data
Mar. 19, 2010 (JP) .................................. 2010-064911

(51) Int. Cl.
A23L 2/02 (2006.01)
A23C 9/123 (2006.01)
A23L 2/38 (2006.01)
A23L 2/52 (2006.01)
C12R 1/25 (2006.01)
A23L 33/135 (2016.01)

(52) U.S. Cl.
CPC .............. *A23C 9/1234* (2013.01); *A23L 2/02* (2013.01); *A23L 2/382* (2013.01); *A23L 2/52* (2013.01); *A23L 33/135* (2016.08); *C12R 1/25* (2013.01); *A23Y 2220/67* (2013.01)

(58) Field of Classification Search
USPC .......................................................... 426/61
See application file for complete search history.

(56) References Cited

U.S. PATENT DOCUMENTS 7,112,346 B2 * 9/2006 Prahl et al. ...................... 426/15
2008/0206403 A1 * 8/2008 Beverini et al. ................ 426/51

FOREIGN PATENT DOCUMENTS

| CN | 101240255 A | 8/2008 |
|---|---|---|
| CN | 101341995 A | 1/2009 |
| CN | 101637291 A | 2/2010 |
| EP | 0 398 957 | 11/1990 |
| EP | 1 508 282 | 2/2005 |
| JP | 5 84065 | 4/1993 |
| JP | 2001 252012 | 9/2001 |
| JP | 2005 6540 | 1/2005 |
| JP | 2005 278517 | 10/2005 |
| JP | 2005 333898 | 12/2005 |
| JP | 2006 296434 | 11/2006 |
| JP | 2008 541774 | 11/2008 |
| WO | WO 2009/099139 | 8/2009 |

OTHER PUBLICATIONS

Kennes, et al., Citrate metabolism by Lactobacillus plantarum isolated from orange juice. Journal of Applied Biotechnology, vol. 70, Issue 5, Mar. 11, 2008.*
Combined Office Action and Search Report issued Sep. 23, 2013 in Chinese Patent Application No. 201180014415.9 (with English translation).
Kimoto, H., "Nyugyo-yo Nyusankin Lactococcus o Probiotics to shite Riyo suru Kokoromi," Kanto Chikusangaku Kaiho, vol. 54, No. 1, pp. 65 to 68, (2004).
Salminen, S., et al., "Demonstration of safety of probiotics—a review," International Journal of Food Microbiology, vol. 44, pp. 93 to 106, (1998).
International Search Report dated Jun. 7, 2011 in PCT/JP11/056065 Filed Mar. 15, 2011.
Combined Chinese Office Action and Search Report dated May 16, 2014 in Patent Application No. 201180014415.9 (with English language translation).
European Search Report in corresponding European Application No. 11756299.1, dated Apr. 20, 2016.

* cited by examiner

*Primary Examiner* — D. Lawrence Tarazano
*Assistant Examiner* — Philip Dubois
(74) *Attorney, Agent, or Firm* — Oblon, McClelland, Maier & Neustadt, L.L.P.

(57) ABSTRACT

Disclosed is a novel lactic acid bacterium belonging to *Lactobacillus plantarum*, which has an excellent fermentative ability affording high achievable cell counts even if various vegetable or fruit juices are used as fermentative substrates. The lactic acid bacterium belonging to *Lactobacillus plantarum* is characterized by the achievable viable cell counts being $10^8$ CFU/ml or more in both cases when 100% juice of grape or of orange is used as fermentative substrate.

11 Claims, No Drawings

SEQUENCE LISTING

<160> NUMBER OF SEQ ID NOS: 2

<210> SEQ ID NO 1
<211> LENGTH: 1501
<212> TYPE: DNA
<213> ORGANISM: Lactobacillus plantarum YIT 0132

<400> SEQUENCE: 1

```
ggcggcgtgc ctaatacatg caagtcgaac gaactctggt attgattggt gcttgcatca      60
tgatttacat ttgagtgagt ggcgaactgg tgagtaacac gtgggaaacc tgcccagaag     120 cggggggataa cacctggaaa cagatgctaa taccgcataa caacttggac cgcatggtcc     180
aagtttgaaa gatggcttcg gctatcactt ttggatggtc ccgcggcgta ttagctagat     240
ggtggggtaa cggctcacca tggcaatgat acgtagccga cctgagaggg taatcggcca     300
cattgggact gagacacggc ccaaactcct acgggaggca gcagtaggga atcttccaca     360
atggacgaaa gtctgatgga gcaacgccgc gtgagtgaag aagggtttcg gctcgtaaaa     420
ctctgttgtt aaagaagaac atatctgaga gtaactgttc aggtattgac ggtatttaac     480
cagaaagcca cggctaacta cgtgccagca gccgcggtaa tacgtaggtg gcaagcgttg     540
tccggattta ttgggcgtaa agcgagcgca ggcggttttt taagtctgat gtgaaagcct     600
tcggctcaac cgaagaagtg catcggaaac tgggaaactt gagtgcagaa gaggacagtg     660
gaactccatg tgtagcggtg aaatgcgtag atatatggaa gaacaccagt ggcgaaggcg     720
gctgtctggt ctgtaactga cgctgaggct cgaaagtatg ggtagcaaac aggattagat     780
accctggtag tccataccgt aaacgatgaa tgctaagtgt tggagggttt ccgcccttca     840
gtgctgcagc taacgcatta agcattccgc ctggggagta cggccgcaag gctgaaactc     900
aaaggaattg acggggcc gcacaagcgg tggagcatgt ggtttaattc gaagctacgc     960
gaagaacctt accaggtctt gacatactat gcaaatctaa gagattagac gttcccttcg    1020
gggacatgga tacaggtggt gcatggttgt cgtcagctcg tgtcgtgaga tgttgggtta    1080
agtcccgcaa cgagcgcaac ccttattatc agttgccagc attaagttgg gcactctggt    1140
gagactgccg gtgacaaacc ggaggaaggt ggggatgacg tcaaatcatc atgcccctta    1200
tgacctgggc tacacacgtg ctacaatgga tggtacaacg agttgcgaac tcgcgagagt    1260
aagctaatct cttaaagcca ttctcagttc ggattgtagg ctgcaactcg cctacatgaa    1320
```

-continued

```
gtcggaatcg ctagtaatcg cggatcagca tgccgcggtg aatacgttcc cgggccttgt   1380
acacaccgcc cgtcacacca tgagagtttg taacacccaa agtcggtggg gtaacctttt   1440
aggaaccagc cgcctaaggt gggacagatg attagggtga agtcgtaaca aggtagccgt   1500
a                                                                    1501
```

<210> SEQ ID NO 2
<211> LENGTH: 1559
<212> TYPE: DNA
<213> ORGANISM: Lactobacillus plantarum YIT 0148

<400> SEQUENCE: 2

```
agagtttgat catggctcag gacgaacgct ggcggcgtgc ctaatacatg caagtcgaac     60
gaactctggt attgattggt gcttgcatca tgatttacat ttgagtgagt ggcgaactgg    120
tgagtaacac gtgggaaacc tgcccagaag cgggggataa cacctggaaa cagatgctaa    180
taccgcataa caacttggac cgcatggtcc aagtttgaaa gatggcttcg gctatcactt    240
ttggatggtc ccgcggcgta ttagctagat ggtggggtaa cggctcacca tggcaatgat    300
acgtagccga cctgagaggg taatcggcca cattgggact gagacacggc ccaaactcct    360
acgggaggca gcagtaggga atcttccaca atggacgaaa gtctgatgga gcaacgccgc    420
gtgagtgaag aagggtttcg gctcgtaaaa ctctgttgtt aaagaagaac atatctgaga    480
gtaactgttc aggtattgac ggtatttaac cagaaagcca cggctaacta cgtgccagca    540
gccgcggtaa tacgtaggtg caagcgttgt ccggatttat tgggcgtaaa gcgagcgca    600 ggcggttttt taagtctgat gtgaaagcct tcggctcaac cgaagaagtg catcggaaac    660
tgggaaactt gagtgcagaa gaggacagtg gaactccatg tgtagcggtg aaatgcgtag    720
atatatggaa gaacaccagt ggcgaaggcg gctgtctggt ctgtaactga cgctgaggct    780
cgaaagtatg ggtagcaaac aggattagat accctggtag tccataccgt aaacgatgaa    840
tgctaagtgt tggagggttt ccgcccttca gtgctgcagc taacgcatta agcattccgc    900
ctggggagta cggccgcaag gctgaaactc aaggaattga cgggggcccg cacaagcgg    960 tggagcatgt ggtttaattc gaagctacgc gaagaacctt accaggtctt gacatactat   1020
gcaaatctaa gagattagac gttcccttcg gggacatgga tacaggtggt gcatggttgt   1080
cgtcagctcg tgtcgtgaga tgttgggtta agtcccgcaa cgagcgcaac ccttattatc   1140
agttgccagc attaagttgg gcactctggt gagactgccg gtgacaaacc ggaggaaggt   1200
ggggatgacg tcaaatcatc atgcccctta tgacctgggc tacacacgtg ctacaatgga   1260
tggtacaacg agttgcgaac tcgcgagagt aagctaatct cttaaagcca ttctcagttc   1320
ggattgtagg ctgcaactcg cctacatgaa gtcggaatcg ctagtaatcg cggatcagca   1380
tgccgcggtg aatacgttcc cgggccttgt acacaccgcc cgtcacacca tgagagtttg   1440
taacacccaa agtcggtggg gtaaccttt aggaaccagc cgcctaaggt gggacagatg    1500
attagggtga agtcgtaaca aggtagccgt aggagaacct gcggctggat cacctccta    1559
```

LACTOBACILLUS CLASSIFIED AS LACTOBACILLUS PLANTARUM, AND USE THEREOF

TECHNICAL FIELD

The present invention relates to a novel lactic acid bacterium that is classified as *Lactobacillus plantarum* suitable for fermentation of various fruit juices as well as to food and drink that contain the same.

BACKGROUND ART

It is considered that in humans noxious organisms such as *Escherichia coli* become dominant with the advancing years and a number of noxious substances produced by the noxious organism have an adverse influence on the human body. Lactic acid bacteria, which are widely separated from the natural world, generate lactic acid in human intestines to keep the intestinal pH acidic to suppress the growth and multiplication of putrefactive bacteria or pathogenic bacteria such as *Escherichia coli* in the intestine and have an effect for making environmental improvements to the intestine. In addition of the effect for making environmental improvements to the intestine, lactic acid bacteria have a useful physiological effect or effects such as constipation improvement effect, protection of infection, enhancement of immunological competence, anti-allergic effect, cancer protective effect, and the like. In this situation, in order to promote health by providing the intestine with these useful bacteria called probiotics, the intake of lactic acid bacteria beverages, fermented milk, or pharmaceutical preparations that contain the live organism of these bacteria have been put into practice.

Lactic acid bacteria used in these lactic acid bacteria beverages, fermented milk, or live organism preparations are those suitable for fermentation of milk materials including ones of yoghurt or cheese origin, specifically including the strain of *Lactobacillus casei, Lactobacillus acidophilus, Lactobacillus bulgaricus, Streptococcus thermophiles, Lactococcus lactis*, and the like.

On the other hand, as the consumer's taste is diversified in recent years, it has been desired to develop a strain capable of using in probiotics in which raw materials other than milk materials, e.g. vegetable juice or fruit juice could be used as fermentative substrates.

However, when the aforementioned strains so far used in production of lactic acid bacteria beverages were utilized in production with vegetable juices or fruit juices as fermentative substrates, it was unable to achieve high viable cell counts for obtaining the effect as probiotics.

Lactic acid bacteria belonging to *Lactobacillus plantarum* have so far been known to have a potent fermentative ability for vegetable juices or fruit juices. For example, *Lactobacillus plantarum* ATCC 14431 is known to achieve the viable cell counts up to $10^7$ CFU/ml or more when a concentrated carrot juice (soluble solid component: 36 mass %; hereinafter simply referred to as %) diluted 6 times is used as a fermentative substrate (Patent Document 1).

In addition, as for a lactic acid bacterium suitable for fermentation of fruit juices in which the organic acid content has been reduced, *Lactobacillus plantarum* 299v (DSM 9843) is known. Although this *Lactobacillus plantarum* 299v (DSM 9843) has such disadvantages as strong post-acidification, remarkable functional defect, and generation of carbon dioxide gas, a technology for suppressing such disadvantages by reducing the organic acid content in the fruit juice is also known (Patent Document 2).

These strains belonging to *Lactobacillus plantanum*, however, do not always afford a high achievable viable cell count concentration to various vegetable juices or fruit juices, and in particular these could not be applied to the fruit juice including grape which is generally considered to be inappropriate as a fermentative substrate for lactic acid bacterium.

PRIOR ART DOCUMENT

Patent Document

Patent document 1: JP-A 2001/252012
Patent document 2: PCT JP-A 2008/541774

SUMMARY OF THE INVENTION

Problem to be Solved by the Invention

Thus, the purpose of the present invention is to provide a novel lactic acid bacterium belonging to *Lactobacillus plantarum* that has an excellent fermentative ability achieving high viable cell counts even if various vegetable juices or fruit juices are used as fermentative substrates as well as to provide food and drink containing the same.

Means for Solving the Problems

The present inventors worked assiduously to solve the aforementioned problems and found that a lactic acid bacterium belonging to *Lactobacillus plantarum* of which the achievable viable cell counts reached $10^8$ CFU/ml or more in any cases, when a certain 100% fruit juice was used as a fermentative substrate, afforded high achievable viable cell counts even if various vegetable juices or fruit juices were used as fermentative substrates. Thus, the invention was completed.

The invention provides a lactic acid bacterium belonging to *Lactobacillus plantarum* of which the achievable viable cell counts are $10^8$ CFU/ml or more in both cases when 100% juice of grape or orange is used as fermentative substrate.

In addition, the invention provides food and drink comprising the aforementioned lactic acid bacterium.

Further, the invention provides a fermentation product which is produced by inoculating and fermenting the aforementioned lactic acid bacterium on food materials.

Furthermore, the invention provides food and drink comprising the aforementioned fermentation product.

Moreover, the invention provides a process for producing a fermentation product which comprises inoculating and fermenting the aforementioned lactic acid bacterium on food materials.

Effect of the Invention

Since the lactic acid bacterium belonging to *Lactobacillus plantarum* of the invention is able to reach viable cell counts of $10^8$ CFU/mL or more when various vegetable juices or fruit juices, particularly fruit juices, are used as fermentative substrates, it can be used in production of food and drink such as beverages used in probiotics based on a variety of fermentative substrates.

In particular, the deposited two strains among the lactic acid bacteria belonging to *Lactobacillus plantarum* of the invention are able to provide food and drink such as beverages of stable quality, since they have no plasmid.

MODE FOR CARRYING OUT THE INVENTION

In this description, 100% fruit juice means those which satisfy the criterion of 100% juice according to the indication standard of quality of fruit juice beverages in the JAS law. In producing the fruit juice, any process may be applied, that is, a process for producing "straight fruit juice" which is produced by thermally treating the juice squeezed from fruits followed by freezing and storing, or a process for producing "concentrated and reconstituting juice" which is produced by evaporating water and concentrating under heating followed by freezing and storing. In "concentrated and reconstituting juice", the concentration rate for the juice is preferably 2 to 10 times, more preferably 3 to 8 times. As far as the criterion of 100% juice is satisfied in the indication standard of quality of fruit juice beverages in the JAS law, sugars, perfume, and/or anti-oxidant may be added.

In this description, the achievable viable cell count means the viable cell count which is achieved by incubating a seed strain on a medium (*Lactobacilli* MRS Broth (made by Difco Co.) sterilized at 121° C. for 15 minutes in an autoclave) as preliminary incubation up to the stationary state, more specifically carrying out the preliminary incubation at 30-37° C. for 16-24 hours, then inoculating 0.4% by volume of the preliminary incubated solution on a fermentative substrate such as 100% juice, followed by incubation at 37° C. for 48 hours. In this connection, the viable count is determined on an MRS agar plate. In addition, the CFU/ml unit indicating the achievable viable cell count represents a colony forming ability when 1 ml is seeded on a culture plate.

In this description, the non-existence of plasmid means that when a plasmid DNA is prepared in a conventional way from 1 ml of fresh *lactobacillus* culture medium, no plasmid DNA is detected under UV irradiation after electrophoresis on 0.7% agarose gel and in subsequent staining of the gel with ethidium bromide.

The lactic acid bacterium belonging to *Lactobacillus plantarum* of the invention (hereinafter referred to as "lactic acid bacterium of the invention") includes those of which the achievable viable cell counts are $10^8$ CFU/ml or more, preferably $10^8$-$10^{10}$ CFU/ml in both cases when 100% juices of grape or orange are used as fermentative substrates.

The lactic acid bacterium of the invention is separated from pickled vegetable, fermented tea, or human feces in a conventional way by separation on an MRS agar plate and screening of the isolated *Lactobacillus plantarum* based on the achievable viable cell counts in the aforementioned fermentative substrates.

From *Lactobacillus plantarum* separated in the aforementioned way, the following 4 strains were obtained.

*Lactobacillus plantarum* YIT 10015 strain
*Lactobacillus plantarum* YIT 0069 strain
*Lactobacillus plantarum* YIT 0148 strain
*Lactobacillus plantarum* YIT 0132 strain Among these 4 strains, YIT 0069, YIT 0148, and YIT 0132 showed the proliferative score values of 25 or more that were obtained by dividing the respective achievable viable cell counts (CFU/ml) by $10^8$ followed by addition, when 100% juices of grape, grape fruit, orange, pineapple or apple were used as fermentative substrates. The proliferative score value is an index for judging whether or not *Lactobacillus plantarum* is suitable for fermentation of fruit juices, and it is preferably 25 or more, more preferably 30-50; since YIT 0148 and YIT 0132 have the proliferative score values of 30-41, they are particularly preferred for use in fermentation of fruit juices.

In this connection, YIT 0132 and YIT 0148 have no plasmid. In general, some of plasmids sometimes have antibiotic resistance, which is transferred to other microorganisms, leading to occurrence of pathogenic bacteria which have antibiotic resistance. In addition, it has not yet been elucidated at present how the gene on the plasmid of which the function is unclear has an influence onto the other microorganism or microorganisms, and therefore it is desirable for the strain to have no plasmid in view of securing safety of the strain. Plasmid is sometimes deleted during subculture or culture, resulting in instability of the form of microorganisms. Since YIT 0132 and YIT 0148 have no plasmid, the stability and quality of the product can be secured.

The strains YIT 0132 and YIT 0148 are respectively named *Lactobacillus plantarum* YIT 0132 and *Lactobacillus plantarum* YIT 0148, and internationally deposited as FERM BP-11349 and FERM BP-11350 as of Feb. 24, 2010, at International Patent Organism Depositary, National Institute of Advanced Industrial Science and Technology, Independent Administrative Agency (Address: Area code 305-8566: Higashi 1-chome 1-banchi 1, chu-o no. 6, Tsukuba City, Ibaragi Pref.). These strains have the following bacteriological properties.

<Bacteriological Properties of *Lactobacilli*: YIT 0132 and YIT 0148 Incubated in *Lactobacilli* MRS Broth at 37° C. for 24 Hours>

(Various Properties)

TABLE 1

| Cell morphology | YIT 0132<br>Rod shape | YIT 0148<br>Rod shape |
| --- | --- | --- |
| Gram staining | + | + |
| Catalase activity | − | − |
| Mobility | − | − |
| Spore | − | − |
| Growth at 15° C. | + | + |
| Growth at 45° C. | − | − |
| Anaerobic growth | + | + |
| Aerobic growth | + | + |
| Generation of gas | − | − |

(Fermentative Properties of Sugars; Measured by API 50CH)

TABLE 2

|  | YIT 0132 | YIT 0148 |
| --- | --- | --- |
| Control | − | − |
| Glycerol | − | − |
| Erythritol | − | − |
| D-Arabinose | − | − |
| L-Arabinose | + | + |
| D-Ribose | + | + |
| D-Xylose | − | − |
| L-Xylose | − | − |
| D-Adonitol | − | − |
| Methyl-β D-xylopyranoside | − | − |
| D-Galactose | + | + |
| D-Glucose | + | + |
| D-Fructose | + | + |
| D-Mannose | + | + |
| L-Sorbose | − | − |
| L-Rhamnose | w | w |
| Dulcitol | − | − |
| Inositol | − | − |

TABLE 2-continued

|  | YIT 0132 | YIT 0148 |
|---|---|---|
| D-Mannitol | + | + |
| D-Sorbitol | + | + |
| Methyl-α D-mannopyranoside | + | + |
| Methyl-α D-glucopyranoside | − | − |
| N-Acethyl glucosamine | + | + |
| Amygdalin | + | + |
| Arbutin | + | + |
| Esculin ferric citrate | + | + |
| Salicin | + | + |
| D-Cellobiose | + | + |
| D-Maltose | + | + |
| D-Lactose | + | + |
| D-Melibiose | + | + |
| D-Sucrose | + | + |
| D-Treharose | + | + |
| Inulin | − | − |
| D-Melezitose | + | + |
| D-Raffinose | + | + |
| Starch | − | − |
| Glycogen | − | − |
| Xylitol | − | − |
| Gentiobiose | + | + |
| D-Turanose | + | + |
| D-Lyxose | − | − |
| D-Tagatose | − | − |
| D-Fucose | − | − |
| L-Fucose | − | − |
| D-Arabitol | − | − |
| L-Arabitol | − | − |
| Gluconate | w | w |
| 2 Keto-gluconate | − | − |
| 5 Keto-gluconate | − | − |

+: positive;
w: weak;
−: negative (16S rDNA)

Using the 16S rDNA base sequence, the strain was identified as follows. Namely, the organism was incubated in an MRS medium at 37° C. for 24 hours, the incubated solution was centrifugally washed, and a DNA was extracted from the organism pellet; the full length of 16S rDNA sequence was amplified by PCR using the extracted DNA as a template, and the base sequence of the amplified product was determined by the Dye Terminator method; the resulting base sequence was searched on a data base to identify the species of the organism. The 16S rDNA base sequences of YIT 0132 and YIT 0148 (SEQ ID No. 1, SEQ ID No. 2) had respectively 99.9% and 99.8% homology with that of *Lactobacillus plantarum* (accession No. D79210), and further it had respectively 99% or more high homology with those of *Lactobacillus paraplantarum* (accession No. AJ306297) and *Lactobacillus pentosus* (accession No. D79211). These 3 species are close relatives to each other, and thus it is not possible to discriminate between them using the 16S rDNA sequence. For discrimination, accordingly, a PCR method in which a species-specific primer targeting the recA gene sequence was used (Appl. Environ. Microbiol., 67, 3450-3454 (2001)) was used with the standard strains of these 3 species as reference. As a result, it was confirmed that YIT 0132 and YIT 0148 were *Lactobacillus plantarum*.

In this connection, in addition to the aforementioned strains as lactic acid bacteria of the invention, it is also possible to utilize any variants of the above strains that exert the same fermentative ability for fruit juices.

The aforementioned lactic acid bacteria of the invention originate in foods and their safety has been confirmed. Thus, they can be utilized in various uses in the same way as the lactic acid bacteria so far used in probiotics, and their ingestion is expected to show a physiological effect such as anti-diarrheal effect.

There is no strict limitation in the amount of the lactic acid bacterium of the invention to be taken in a human or animal, and the preferred dose is $10^5$ CFU-$10^{13}$ CFU for a day as viable cell counts, particularly $10^8$ CFU-$10^{12}$ CFU. The lactic acid bacterium of the invention is preferably taken continuously, but it may be taken at certain intervals, for example, every other month, every other week, every other day, or taken within a short period of time.

In order to attain the physiological effect of the lactic acid bacterium of the invention, for example, it may be utilized as a conventional pharmaceutical preparation which is prepared by mixing with a solid or liquid pharmaceutically acceptable innoxious carrier. Such a pharmaceutical preparation includes, for example, solid preparation such as tablets, granules, powders, capsules, and the like, liquid preparation such as solutions, suspensions, emulsions, and the like, and lyophilized preparations. These preparations may be prepared according to pharmaceutically conventional ways. The aforementioned pharmaceutically innoxious carrier includes, for example, glucose, lactose, sucrose, starch, mannitol, dextrin, fatty acid glyceride, polyethylene glycol, hydroxyethyl starch, ethylene glycol, polyoxyethylene sorbitan fatty acid ester, amino acid, gelatin, albumin, water, physiological saline, and the like. In addition, if required, a conventional additive such as stabilizer, wetting agent, emulsifying agent, binding agent, tonicity adjusting agent, diluent, and the like may properly be added.

The lactic acid bacterium of the invention may be not only formulated into the aforementioned pharmaceutical preparations but also added into solid or liquid food and drink. When added into food and drink, it may be added alone or together with various nutritious ingredients. Practically, when the lactic acid bacterium of the invention is added into food and drink, an additive which can be used as food and drink may preferably be used and formulated in a conventional way into an edible form, that is, granular form, grain form, tablets, capsules, paste, and the like. The sorts of food and drink are, for example, processed meat products such as ham, sausage, etc., processed marine products such as boiled fish paste, tube-shaped fish paste cake, etc., food such as bread, cake, butter, milk powder, and the like, as well as water, beverage such as fruit juice, milk, refreshing drink, and tea drink. In this connection, the food and drink include livestock feed.

In addition, the food and drink suitably utilizable for the lactic acid bacterium of the invention include fermented milk, fermented soymilk, fermented fruit juice, fermented vegetable juice, and the like, which are obtained by inoculating the lactic acid bacterium onto various food materials such as animal milk, soymilk, fruit juice, vegetable juice, and the like, followed by fermentation. Above all, a beverage containing fermented fruit juice is particularly preferred. This type of food and drink is preferred since it contains the lactic acid bacterium in a viable state.

The food and drink containing the above fermented product such as fermented milk, fermented soymilk, fermented fruit juice and fermented vegetable juice may be produced according to a conventional way. Specifically, in producing a fermented fruit juice beverage with a lactic acid bacterium of the invention, a lactic acid bacterium of the invention is first inoculated alone or together with another microorganism onto fruit juice which is sterilized under a condition suitable for the juice to be used, followed by incubation; the product is homogenized to give a fermented juice base. This fermented juice base is then mixed with a beverage containing 100% fruit juice, syrup or other unfermented juice, to which is then added a flavor and so on, yielding a final product.

The fruit juices used as raw materials for the aforementioned fermented fruit juice beverages include but are not limited to juices of grape, grapefruit, orange, pineapple, apple, and the like, particularly fruit juices of orange and apple are preferred.

The fermented vegetable juice beverage may also be produced in the same way as the aforementioned fermented fruit juice beverage. The vegetable juices used as raw materials for the aforementioned fermented vegetable juice beverages include but are not limited to juices of carrot, e.g. carrot, Murasaki ninjin (carrot); sweet potato, e.g. Ayamurasaki, J-Red; kale; and tomato, and particularly vegetable juices of carrot, Ayamurasaki, and J-Red are preferred.

The fermented fruit juice beverage and vegetable juice beverage may be combined with an optional ingredient such as sweetening agent such as syrup, emulsifying agent, thickener (stabilizer), various vitamins, and the like. The syrup includes sugars, e.g. glucose, sucrose, fructose, fructose-glucose solution, glucose-fructose solution, palatinose, trehalose, lactose, xylose, maltose, honey, syrup; sugar alcohols, e.g. sorbitol, xylitol, erythritol, lactitol, palatinit, reduced glutinous starch syrup, reduced malt glutinous starch syrup; and highly sweet sweetening agents, e.g. aspartame, thaumatin, sucralose, acesulfame K, stevia, and the like. Additionally, vitamin, e.g. vitamin A, vitamins B, vitamin C, vitamins E; mineral, e.g. calcium, magnesium, zinc, iron, manganese; acid tasting agent, e.g. citric acid, lactic acid, acetic acid, malic acid, tartaric acid, gluconic acid; milk fat, e.g. cream, butter, sour cream; flavor, e.g. yogurt-type, berry-type, orange-type, Chinese quince-type, perilla-type, citrus-type, apple-type, mint-type, grape-type, apricot-type, pear, custard cream, peach, melon, banana, tropical, herb-type, black tea, coffee; herb extract; brown sugar extract; and the like may be combined.

In producing a fermented fruit or vegetable juice beverage, a microorganism or microorganisms other than the lactic acid bacteria of the invention may be used at the same time. Such a microorganism includes, for example, *Bifidobacterium bacterium* such as *Bifidobacterium breve*, *Bifidobacterium longum*, *Bifidobacterium bifidum*, *Bifidobacterium animalis*, *Bifidobacterium suis*, *Bifidobacterium infantis*, *Bifidobacterium adolescentis*, *Bifidobacterium catenulatum*, *Bifidobacterium pseudocatenulatum*, *Bifidobacterium lactis*, *Bifidobacterium globosum*, and so on; *Lactobacillus bacterium* such as *Lactobacillus casei*, *Lactobacillus acidophilus*, *Lactobacillus buchneri*, *Lactobacillus gallinarum*, *Lactobacillus amylovorus*, *Lactobacillus brevis*, *Lactobacillus rhamnosus*, *Lactobacillus kefir*, *Lactobacillus paracasei*, *Lactobacillus crispatus*, *Lactobacillus zeae*, *Lactobacillus helveticus*, *Lactobacillus salivalius*, *Lactobacillus gasseri*, *Lactobacillus fermentum*, *Lactobacillus reuteri*, *Lactobacillus delbrueckii* subsp. *Bulgaricus*, *Lactobacillus delbrueckii* subsp. *Delbrueckii*, *Lactobacillus johnsonii*, *Lactobacillus pentosus*, *Lactobacillus paraplantarum*, and so on; *Streptococcus bacterium* such as *Streptococcus thermophiles*, and so on; *Lactococcus bacterium* such as *Lactococcus lactis* subsp. *Lactis*, *Lactococcus lactis* subsp. *Cremoris*, and so on; *Enterococcus bacterium* such as *Enterococcus faecalis*, *Enterococcus faecium*, and so on; *Bacillus bacterium* such as *Bacillus subtilis*; yeast belonging to *Saccharomyses* or *Torulaspora* or *Candida* such as *Saccharomyses cerevisiae*, *Torulaspora delbrueckii*, *Candida kefyr*, and so on.

EXAMPLES

The invention will be explained in more detail by the following examples but are not intended to limit the scope of the invention.

Example 1

Fermentation Test for Fruit Juice by Various Lactic Acid Bacterium (1) Strain

In order to find out a strain having high fermentative ability for fruit juice, the 43 strains of *lactobacilli* as shown in Table 3 were selected for the test, which strains were mainly isolated from fruit trees.

(2) Seed Organisms and Incubation

*Lactobacilli* MRS Broth (Difco Co.) was sterilized in an autoclave at 121° C. for 15 minutes, on which the strains were then inoculated. Since *Sporolactobacillus* species had to be incubated in an anaerobic condition, the vessel was filled with $N_2$ atmosphere and tightly closed with a butyl rubber stopper. Since other species are aerobes, the vessel was capped with an aluminum cap and incubated at 30° C. for 16 hours until reaching a stationary state.

(3) Proliferative Property with Fruit Juice

Commercially available concentrated reduced 100% juices (grape juice (Dole Ltd.) and orange juice (Yakult Honsha)) were respectively distributed aseptically into test tubes, onto which 0.4% volume of cell solution was inoculated, and incubated at 37° C. for 48 hours.

(4) Measurement of Viable Cell Counts

The incubated solution was properly diluted with a sterilized diluent (0.1% yeast extract solution) and applied on an MRS agar plate with a spiral system, and the viable cell counts were measured. The proliferative property of the tested 43 strains in the fruit juices was investigated. The results are shown in Table 3.

(5) Investigation of Proliferative Property in the Fruit Juices

Most of the organisms showed no proliferation in grape juice, but only the 2 strains of *Lactobacillus plantarum* grew well, where the viable cell counts increased to $1 \times 10^8$ CFU/ml. In case of orange juice, most organisms except a few strains grew, and the viable cell counts reached $1 \times 10^7$ CFU/ml or more. No growth was observed in all strains of *Sporolactobacillus* anaerobically incubated both in grape juice and orange juice. From the above results, it was elucidated that, when grape juice and orange juice were used as fermentative substrates, the lactic acid bacterium showing the achievable viable cell counts up to $1 \times 10^8$ CFU/ml is only *Lactobacillus plantarum*.

TABLE 3

| | Species | Strain | Culture method | Grape juice Viable cell counts (CFU/ml) | Orange juice Viable cell counts (CFU/ml) |
|---|---|---|---|---|---|
| 1 | *Lactococcus lactis* | YIT 10176 | Aerobic | — | $3.86 \times 10^7$ |
| 2 | *Lactococcus lactis* | YIT 10177 | Aerobic | — | $3.86 \times 10^7$ |
| 3 | *Lactococcus lactis* | YIT 10178 | Aerobic | — | $6.71 \times 10^7$ |
| 4 | *Lactococcus lactis* | YIT 10179 | Aerobic | $6.10 \times 10^7$ | $6.10 \times 10^7$ |
| 5 | *Lactococcus lactis* | YIT 10180 | Aerobic | $7.93 \times 10^7$ | $7.93 \times 10^7$ |

TABLE 3-continued

| # | Species | Strain | Culture method | Grape juice Viable cell counts (CFU/ml) | Orange juice Viable cell counts (CFU/ml) |
|---|---|---|---|---|---|
| 6 | Lactococcus lactis | YIT 10183 | Aerobic | — | $4.67 \times 10^7$ |
| 7 | Lactobacillus brevis | YIT 10184 | Aerobic | — | — |
| 8 | Lactococcus lactis | YIT 10185 | Aerobic | — | $9.15 \times 10^7$ |
| 9 | Lactococcus lactis | YIT 10186 | Aerobic | — | $2.64 \times 10^7$ |
| 10 | Leuconostoc fallax | YIT 10187 | Aerobic | — | $4.10 \times 10^6$ |
| 11 | Lactococcus lactis | YIT 10188 | Aerobic | $3.86 \times 10^7$ | $3.86 \times 10^7$ |
| 12 | Weissella paramesenteroides | YIT 10189 | Aerobic | — | — |
| 13 | Lactobacillus plantarum | YIT 0132 | Aerobic | $1.57 \times 10^8$ | $7.71 \times 10^8$ |
| 14 | Lactobacillus plantarum | YIT 0148 | Aerobic | $1.42 \times 10^8$ | $6.06 \times 10^8$ |
| 15 | Leuconostoc mesenteroides | YIT 10192 | Aerobic | — | $3.76 \times 10^8$ |
| 16 | Leuconostoc mesenteroides | YIT 10193 | Aerobic | — | $3.85 \times 10^8$ |
| 17 | Lactobacillus casei | YIT 10194 | Aerobic | $1.02 \times 10^7$ | $1.46 \times 10^8$ |
| 18 | Lactobacillus casei | YIT 10195 | Aerobic | $2.03 \times 10^7$ | $1.25 \times 10^8$ |
| 19 | Leuconostoc mesenteroides | YIT 10196 | Aerobic | $2.24 \times 10^7$ | — |
| 20 | Lactobacillus animalis | YIT 10197 | Aerobic | — | — |
| 21 | Leuconostoc mesenteroides | YIT 10198 | Aerobic | — | — |
| 22 | Lactococcus lactis | YIT 10199 | Aerobic | — | $4.47 \times 10^7$ |
| 23 | Lactococcus lactis | YIT 10200 | Aerobic | — | $5.18 \times 10^7$ |
| 24 | Lactococcus lactis | YIT 10201 | Aerobic | — | $5.08 \times 10^7$ |
| 25 | Lactococcus lactis | YIT 10202 | Aerobic | $4.06 \times 10^6$ | — |
| 26 | Lactococcus lactis | YIT 10203 | Aerobic | — | $1.52 \times 10^8$ |
| 27 | Lactococcus lactis | YIT 10204 | Aerobic | — | — |
| 28 | Lactococcus lactis | YIT 10205 | Aerobic | $4.06 \times 10^6$ | $3.86 \times 10^7$ |
| 29 | Lactococcus lactis | YIT 10206 | Aerobic | — | — |
| 30 | Sporolactobacillus kofuensis | YIT 10214 | Aerobic | $6.09 \times 10^6$ | $8.94 \times 10^7$ |
| 31 | Lactococcus lactis | YIT 10219 | Aerobic | — | $1.63 \times 10^7$ |
| 32 | Lactococcus lactis | YIT 10220 | Aerobic | — | $7.93 \times 10^7$ |
| 33 | Lactococcus lactis | YIT 10221 | Aerobic | — | $5.69 \times 10^7$ |
| 34 | Sporolactobacillus inulinus | YIT 10207 | Anaerobic | — | — |
| 35 | Sporolactobacillus nakayamae | YIT 10208 | Anaerobic | — | — |
| 36 | Sporolactobacillus nakayamae | YIT 10210 | Anaerobic | — | — |
| 37 | Sporolactobacillus nakayamae | YIT 10211 | Anaerobic | — | — |
| 38 | Sporolactobacillus nakayamae | YIT 10212 | Anaerobic | — | — |
| 39 | Sporolactobacillus kofuensis | YIT 10215 | Anaerobic | — | — |
| 40 | Sporolactobacillus kofuensis | YIT 10216 | Anaerobic | — | — |
| 41 | Sporolactobacillus kofuensis | YIT 10217 | Anaerobic | — | — |
| 42 | Sporolactobacillus kofuensis | YIT 10218 | Anaerobic | — | — |
| 43 | Sporolactobacillus inulinus | YIT 10222 | Anaerobic | — | — |

*The symbol (—) indicates the viable cell counts being less than detection limit ($2 \times 10^6$ CFU/ml).

Example 2

Fermentation Test for Fruit Juice by *Lactobacillus plantarum*

(1) Strain

The 12 strains of *Lactobacillus plantarum* were targeted. The origin of these strains were: YIT 0220 strain from ATCC 14431, Y 50097 strain from commercially available fermented milk, YIT 0102 strain from a standard strain (ATCC 14917), and Y 99005 strain, 299v strain isolated from a milk product. The others were isolated from pickles, fermented tea, and human feces.

(2) Seed Organisms and Incubation

*Lactobacilli* MRS Broth (Difco Co.) was distributed into small test tubes and sterilized in an autoclave at 121° C. for 15 minutes, on which the organisms were then inoculated. The test tubes were capped with aluminum caps and incubated at 37° C. for 16 hours until reaching a stationary state.

(3) Proliferative Property with Fruit Juice

Commercially available concentrated reduced 100% juices (grape juice (Dole Ltd.), grape fruit juice (Yakult Honsha), orange juice (Yakult Honsha), pineapple juice (Yakult Honsha), and apple juice (Yakult Honsha)) were respectively distributed aseptically into test tubes, onto which 0.4% volume of organism solution was inoculated, and incubated at 37° C. for 48 hours.

(4) Measurement of Viable Cell Counts

The culture solution was properly diluted with a sterilized diluent (0.1% yeast extract solution) and applied on an MRS agar plate with a spiral system, and the viable cell counts were measured. Table 4 shows the results. The proliferative score values in the fruit juices were calculated by dividing the respective achievable viable cell counts (CFU/ml) by $10^8$ followed by addition, when 100% juices of grape, grape fruit, orange, pineapple and apple were used as fermentative substrates. The results are also shown in Table 4.

(5) Investigation of Proliferative Property in the Fruit Juices

When 100% juices of grape and pineapple were used as fermentative substrates, the following 4 strains showed the achievable viable cell counts of $10^8$ CFU/ml or more in both cases: YIT 10015, YIT 0069, YIT 0148 and YIT 0132. As a result, the 3 strains, YIT 0069 (proliferative score: 27), YIT 0148 (proliferative score: 30) and YIT 0132 (proliferative score: 41), showed markedly higher proliferative score than the standard strain YIT 0102 of *Lactobacillus plantarum* (proliferative score: 14), the strains YIT 0220 (proliferative score: 10) and Y99005 (proliferative score: 18) which are known to have a fermentative ability with vegetable juices and fruit juices.

TABLE 4

| | Grape | Grape fruit | Orange | Pineapple | Apple | Prolif. score |
|---|---|---|---|---|---|---|
| YIT 0012 | $2.03 \times 10^6$ | $<2.03 \times 10^6$ | $<2.03 \times 10^6$ | $<2.03 \times 10^6$ | $<2.03 \times 10^6$ | <1 |
| YIT 10023 | $2.03 \times 10^6$ | $4.07 \times 10^6$ | $6.10 \times 10^6$ | $6.50 \times 10^7$ | $7.11 \times 10^7$ | 1 |
| YIT 0032 | $2.44 \times 10^7$ | $1.02 \times 10^7$ | $3.62 \times 10^8$ | $4.47 \times 10^7$ | $2.03 \times 10^7$ | 5 |
| YIT 0220 | $8.13 \times 10^6$ | $8.13 \times 10^6$ | $2.49 \times 10^8$ | $3.43 \times 10^8$ | $3.69 \times 10^8$ | 10 |
| Y 50097 | $1.42 \times 10^7$ | $2.44 \times 10^7$ | $3.56 \times 10^8$ | $5.92 \times 10^8$ | $2.45 \times 10^8$ | 12 |
| YIT 10015 | $1.09 \times 10^8$ | $3.25 \times 10^7$ | $4.35 \times 10^8$ | $3.54 \times 10^8$ | $3.31 \times 10^8$ | 13 |
| YIT 0102 | $2.03 \times 10^7$ | $9.30 \times 10^7$ | $4.04 \times 10^8$ | $5.58 \times 10^8$ | $2.82 \times 10^8$ | 14 |
| Y 99005 | $8.89 \times 10^7$ | $1.80 \times 10^8$ | $4.28 \times 10^8$ | $7.51 \times 10^8$ | $3.56 \times 10^8$ | 18 |
| YIT 10021 | $9.35 \times 10^7$ | $3.25 \times 10^7$ | $4.92 \times 10^8$ | $8.57 \times 10^8$ | $4.11 \times 10^8$ | 19 |
| YIT 0069 | $2.02 \times 10^8$ | $8.33 \times 10^7$ | $8.55 \times 10^8$ | $1.07 \times 10^9$ | $4.44 \times 10^8$ | 27 |
| YIT 0148 | $4.07 \times 10^8$ | $1.68 \times 10^8$ | $8.23 \times 10^8$ | $1.20 \times 10^9$ | $3.90 \times 10^8$ | 30 |
| YIT 0132 | $3.17 \times 10^8$ | $2.04 \times 10^8$ | $1.25 \times 10^9$ | $1.85 \times 10^9$ | $4.42 \times 10^8$ | 41 |

Unit: CFU/ml

Example 3

Confirmation of the Existence of Plasmid in *Lactobacillus plantarum* Strain
(1) Strains and Incubation
The strain was incubated on an MRS medium at 37° C. for 20 hours.
(2) Preparation of Plasmid DNA
The organism was collected from 1 ml of fresh incubated solution by centrifugation at 3,000×g, and suspended into 200 μl of lysis solution (50 μg/ml N-acetylmuramidase SG, 3 mg/ml egg lysozyme, 100 μg/ml RNase A, 50 mM Tris-HCl (pH 8.0), 10 mM EDTA). This was kept at 37° C. for 30 minutes to form a protoplast. The protoplast-formed organism was collected at 3,000×g and treated with a commercially available kit (BioRad Miniprep.) for preparing a plasmid by an alkali method to yield a plasmid DNA.
(3) Detection of Plasmid
The plasmid DNA was subjected to electrophoresis on 0.7% agarose gel, which was then stained with ethidium bromide and photographed under UV irradiation to evaluate the existence of plasmid. The results are shown in Table 5.
(4) Existence of Plasmid
The 7 strains which showed a good juice-fermentative ability in Example 2 were selected for investigation. In 5 of the 7 strains, plasmids were observed. Among these strains, YIT 0132 and YIT 0148 both had no plasmid, which strains showed the achievable viable cell counts of $10^8$ CFU/ml or more with grape juice and grape fruit juice in Example 2.

TABLE 5

| Strain | Existence of plasmid |
|---|---|
| YIT 10023 | + |
| YIT 0102 | + |
| YIT 10021 | + |
| YIT 10015 | + |
| Y 99005(299v) | + |
| YIT 0132 | − |
| YIT 0148 | − |

+: existence of plasmid
−: non-existence of plasmid

Example 4

Lactic Acid Bacteria Beverages (1):
Fruit juice or vegetable juice adjusted at Brix (Bx) 10 as shown in Table 6 was sterilized in a condition as described in Table 6. After cooling, *Lactobacillus plantarum* YIT 0132 pre-incubated in an MRS broth was inoculated thereon at 0.4%, and incubated at 37° C. for 48 hours. For the resulting fermented fruit juice or vegetable juice, the viable cell counts at the time of production were measured on an MRS agar plate (Table 6). In addition, the taste of these lactic acid bacteria beverages was evaluated freely, indicating that all were appropriate for drinking. In particular, orange, apple, carrot, Ayamurasaki, and J-Red had good taste.

TABLE 6

| Food Material | Condition for Sterilization | pH After Sterilization | Viable Cell Count at the Time of Production* |
|---|---|---|---|
| Orange | 110° C. 3 sec. | 3.77 | $8.9 \times 10^8$ |
| Apple | | 3.80 | $3.5 \times 10^8$ |
| Pineapple | | 3.61 | $1.0 \times 10^9$ |
| Peach | | 3.94 | $5.1 \times 10^8$ |
| Carrot | 135° C. 1 min | 6.08 | $1.6 \times 10^9$ |
| Murasakininjin | 123° C. 1 min | 4.26 | $1.7 \times 10^9$ |
| Ayamurasaki | 135° C. 1 min | 6.08 | $9.0 \times 10^8$ |
| J-Red | | 5.68 | $1.8 \times 10^9$ |
| Kale | | 5.87 | $3.7 \times 10^9$ |
| Tomato juice** | 130° C. 3 sec | 4.30 | $1.9 \times 10^9$ |
| Tomato puree | 123° C. 1 min | 4.30 | $1.9 \times 10^9$ |

*Unit: CFU/ml
**Prepared by squeezing tomato, removal of pulp by centrifugation, and concentration Example 5

Lactic Acid Bacteria Beverages (2):
Skim milk (10%) and yeast extract (0.03%) were dissolved in warm water, and sterilized at 135° C. for 3 seconds. After cooling, *Lactobacillus plantarum* YIT 0132 pre-incubated on an MRS broth was inoculated thereon at 0.4%, and incubated at 37° C. for 48 hours. The resulting lactic acid bacteria beverage had the viable cell counts of $5.2 \times 10^8$ CFU/ml at the time of production on an MRS agar plate. The taste was moderately acidic, making drinking easy.

Example 6

Lactic Acid Bacteria Beverages (3):
Fruit juice or vegetable juice adjusted at Brix (Bx) 10 as shown in Table 7 was sterilized in a condition as described in Table 7. *Lactobacillus plantarum* YIT 0148 pre-incubated in an MRS broth was inoculated thereon at 0.4%, and incubated at 37° C. for 48 hours. For the resulting fermented fruit juice or vegetable juice, the viable cell counts at the time of production were measured on an MRS agar plate (Table 7). In addition, the taste of these lactic acid bacteria beverages was evaluated freely, indicating that all were appropriate for drinking. In particular, orange, apple, carrot, Ayamurasaki, and J-Red had good taste.

TABLE 7

| Food Material | Condition for Sterilization | pH After Sterilization | Viable Cell Count at the Time of Production* |
|---|---|---|---|
| Orange | 110° C. 3 sec. | 3.77 | $7.9 \times 10^8$ |
| Apple | | 3.80 | $2.4 \times 10^8$ |
| Pineapple | | 3.61 | $1.0 \times 10^9$ |
| Peach | | 3.94 | $6.1 \times 10^8$ |
| Carrot | 135° C. 1 min | 6.08 | $1.9 \times 10^9$ |
| Murasakininjin | 123° C. 1 min | 4.26 | $1.6 \times 10^9$ |
| Ayamurasaki | 135° C. 1 min | 6.08 | $3.5 \times 10^8$ |
| J-Red | | 5.68 | $1.1 \times 10^9$ |
| Kale | | 5.87 | $1.3 \times 10^9$ |
| Tomato juice** | 130° C. 3 sec | 4.30 | $1.7 \times 10^9$ |
| Tomato puree | 123° C. 1 min | 4.30 | $1.6 \times 10^9$ |

*Unit: CFU/ml
**Prepared by squeezing tomato, removal of pulp by centrifugation, and concentration Example 7

Lactic Acid Bacteria Beverages (4):

Skim milk (10%) and yeast extract (0.03%) were dissolved in warm water, and sterilized at 135° C. for 3 seconds. After cooling, *Lactobacillus plantarum* YIT 0148 pre-incubated on an MRS broth was inoculated thereon at 0.4%, and incubated at 37° C. for 48 hours. The resulting lactic acid bacteria beverage had the viable cell counts of $3.2 \times 10^8$ CFU/ml at the time of production on an MRS agar plate. The taste was moderately acidic, making drinking easy.

INDUSTRIAL APPLICABILITY

The lactic acid bacteria of the invention show high achievable viable cell counts even if various vegetable or fruit juices are used as fermentative substrates. Thus, the lactic acid bacteria of the invention can be used suitably in probiotics.

The invention claimed is:

1. A fermented fruit juice comprising a lactic acid bacterium belonging to *Lactobacillus plantarum*,
   wherein achievable viable cell counts of the bacterium are $10^8$ CFU/ml or more in both cases when a solution of the bacterium pre-incubated on *Lactobacilli* MRS Broth at 37° C. for 16 hours up to the stationary state is inoculated at 0.4% volume on 100% juice of grape or of orange as a fermentative substrate and incubated at 37° C. for 48 hours,
   wherein the lactic acid bacterium is *Lactobacillus plantarum* YIT 0132 (FERM BP-11349) or *Lactobacillus plantarum* YIT 0148 (FERM BP-11350).

2. The fermented fruit juice of claim 1, wherein the lactic acid bacterium has no plasmid.

3. The fermented fruit juice of claim 1, wherein the *Lactobacillus plantarum* has a proliferative score value calculated by dividing respective achievable viable cell counts (CFU/ml) by $10^8$ followed by addition is 25 or more, when a solution of the bacterium pre-incubated on *Lactobacilli* MRS Broth at 37° C. for 16 hours up to the stationary state is inoculated at 0.4% volume on 100% juice of grape, grape fruit, orange, pineapple or apple as fermentative substrate, respectively, and incubated at 37° C. for 48 hours.

4. A method of producing the fermented fruit juice of claim 1 comprising inoculating and fermenting a fruit juice with *Lactobacillus plantarum* YIT 0132 (FERM BP-11349) or *Lactobacillus plantarum* YIT 0148 (FERM BP-11350).

5. A food or drink product comprising a fermented juice obtained by fermenting fruit juice with at least one *Lactobacillus plantarum* selected from the group consisting of *Lactobacillus plantarum* YIT 0132 (FERM BP-11349) and *Lactobacillus plantarum* YIT 0148 (FERM BP-11350).

6. The food or drink product of claim 5, which is a food product.

7. The food or drink product of claim 5, which is a drink product.

8. The food or drink product of claim 5, wherein the *Lactobacillus plantarum* is *Lactobacillus plantarum* YIT 0132 (FERM BP-11349).

9. The food or drink product of claim 5, wherein the *Lactobacillus plantarum* is *Lactobacillus plantarum* YIT 0148 (FERM BP-11350).

10. The food or drink product of claim 5, wherein the *Lactobacillus plantarum* has no plasmid.

11. A method of making the food or drink product of claim 5, comprising inoculating and fermenting a food or drink with the *Lactobacillus plantarum*.

* * * * *